United States Patent [19]

Scotese et al.

[11] 4,245,094

[45] Jan. 13, 1981

[54] 5-AMINO-2,8-DIALKYL-7,8-DIHYDRO-7-OXO-PYRIDO-[2,3-d]PYRIMIDINE-6 CARBOXYLIC ACID DERIVATIVES

[75] Inventors: Anthony C. Scotese, King of Prussia; Robert L. Morris, Devon; Arthur A. Santilli, Havertown, all of Pa.

[73] Assignee: American Home Products Corporation, New York, N.Y.

[21] Appl. No.: 116,123

[22] Filed: Jan. 28, 1980

[51] Int. Cl.$^3$ .................. A61K 31/505; C07D 471/04
[52] U.S. Cl. ..................................... 544/279; 424/251
[58] Field of Search ......................................... 544/279

[56] References Cited

U.S. PATENT DOCUMENTS

| | | | |
|---|---|---|---|
| 3,320,252 | 5/1967 | Lesher | 544/279 |
| 3,673,184 | 6/1972 | Minami et al. | 544/279 |
| 3,992,380 | 11/1976 | Lesher et al. | 544/279 |

Primary Examiner—Donald G. Daus
Assistant Examiner—James H. Turnipseed
Attorney, Agent, or Firm—Richard K. Jackson

[57] ABSTRACT

The 5-amino-2,8-dialkyl-7,8-dihydro-7-oxo-pyrido[2,3-d]-pyrimidine-6-carboxylic acid derivatives of the invention are anti-secretory agents.

4 Claims, No Drawings

5-AMINO-2,8-DIALKYL-7,8-DIHYDRO-7-OXO-PYRIDO-[2,3-d]PYRIMIDINE-6 CARBOXYLIC ACID DERIVATIVES

BRIEF DESCRIPTION OF THE INVENTION

In accordance with this invention there is provided a group of 5-amino-2,8-dialkyl-7,8-dihydro-7-oxo-pyrido[2,3-d]pyrimidine-6-carboxylic acid derivatives which act as gastric anti-secretory agents, by virtue of which they are useful in the treatment of peptic ulcer disease.

As anti-secretory agents, the compounds of this invention reduce (1) total gastric volume, (2) hydrogen ion secretion, or (3) hydrogen ion concentration. The reduction of any one of these parameters aids in attenuating the general debilitating influence of a peptic ulcer in humans. The use of compounds exhibiting anti-secretory activity in the curative and/or prophylactic treatment of peptic ulcer disease is an established, beneficial procedure.

DETAILED DESCRIPTION OF THE INVENTION

The 5-amino-2,8-dialkyl-7,8-dihydro-7-oxo-pyrido[2,3-d]pyrimidine-6-carboxylic acid gastric anti-secretory agents of this invention are depicted by the structural formula:

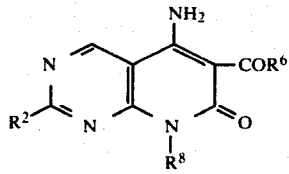

in which $R^2$ is alkyl of 1 to 6 carbon atoms;

$R^6$ is alkoxy of 1 to 6 carbon atoms, amino, mono- and di-alkylamino where each alkyl group contains from 1 to 6 carbon atoms, 2-hydroxyethylamino, 2-alkoxyethylamino of 3 to 8 carbon atoms or 2-(dialkylamino)ethylamino in which each alkyl group contains from 1 to 6 carbon atoms; and $R^8$ is alkyl of 1 to 6 carbon atoms;

or a pharmaceutically acceptable salt thereof.

The compounds of this invention, are produced by reaction of the sodio salt of diethyl malonate with a 4-amino-5-cyano-2-alkyl-pyrimidine followed by alkylation according to the equation:

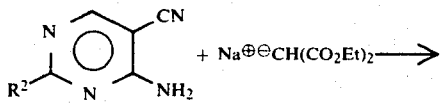

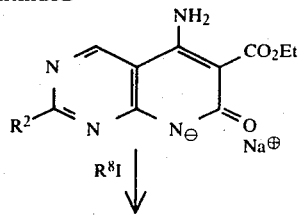

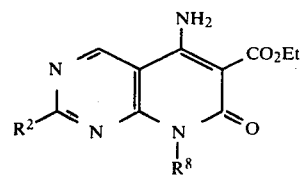

By analogy, employing, as the initial reactant, a 4-alkylamino-5-cyano-2-alkyl-pyrimidine, the alkyl group in 4-position of the pyrimidine reactant is carried through the reaction sequence to appear as $R^8$ in the final product. Furthermore, the 4-alkylamino-5-cyano-2-alkyl-pyrimidine reactants may be acylated with ethyl malonyl chloride to afford the corresponding ethyl malonamides which may be cyclized under Dieckmann conditions to obtain the desired products. The resulting ester group in 6-position of the pyrido pyrimidine products is readily converted by known techniques to an amide

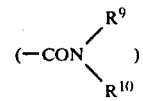

by reaction with an amine

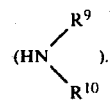

The starting materials are either known compounds or are prepared by conventional methods described in the chemical literature. In the preceding equation the substituents designated $R^2$ and $R^8$ are defined in the description of the compounds of the invention. The group

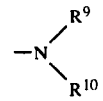

is an amine in which $R^9$ and $R^{10}$ are independently hydrogen or alkyl of 1 to 6 carbon atoms and when $R^9$ is hydrogen $R^{10}$ is 2-(dialkylamino)ethyl in which each alkyl group contains from 1 to 6 carbon atoms, 2-hydroxyethyl or 2-alkoxyethyl of 3 to 8 carbon atoms.

Each of the anti-secretory agents of this invention is active in the following scientifically recognized, standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally (i.d.). The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr.) and acid concentration (mEq/L) estimates the total acid output (TAO, mEq/4 hr.) over the four-hour test period. An analysis of variance is performed on these data to determine statistically significant ($p < 0.05$) deviation between control versus drug-treated groups.

Thus, the compounds disclosed herein are useful in the treatment of peptic ulcer disease. The dosage regimen will vary with the mode of administration, size and age of the subject treated as well as the severity of the dysfunction. Thus, administration of the compounds of this invention must be under the guidance and instruction of a physician.

The compounds of this invention may be administered by conventional oral or parenteral routes as solids, liquids or nubulized suspensions. Conventional adjuvants known to the art may be combined with the antisecretory agents of this invention to provide compositions and solutions for administrative purposes, although it is considered desirable and feasible to use neat or put compounds without additives other than for the purpose of providing suitable pharmaceutically acceptable solutions. Toward that end, those compounds which contain a basic amino substituent may be converted to pharmaceutically acceptable salts with such acids as hydrochloric, hydrobromic, sulfuric, methane sulfonic, nitric, p-toluene sulfonic acetic, citric, maleic, succinic acid, and the like.

The following examples are presented to illustrate the production of representative compound of this invention. After each example, the anti-secretory activity expressed as the percent inhibition of gastric total acid output at a dose of 32 milligrams per kilogram intraduodenal (i.d.) is presented for the exemplified compound. The melting points (m.p.) for the exemplified products is given in degrees Centigrade.

EXAMPLE 1

5-Amino-7,8-dihydro-8-ethyl-2-methyl-7-oxo-pyrido[2,3-d]pyrimidine-6-carboxylic acid ethyl ester To a solution of 3.45 g. (0.15 g. atom) of sodium in 500 ml. of ethanol was added 24.0 g. (0.15 mole) of diethyl malonate followed by 6.7 g. (0.15 mole) 4-amino-2-methyl-5-pyrimidinecarbonitrile. The reaction mixture was heated under reflux with stirring for 17 hours. The resulting filter cake was removed by filtration to obtain the sodium salt of 5-amino-7,8-dihydro-2-methyl-7-oxo-pyrido[2,3-d]pyrimidine-6-carboxylic acid ethyl ester.

To a solution containing 5.4 g. (0.02 mole) of the sodium salt of 5-amino-7,8-dihydro-2-methyl-7-oxo-pyrido[2,3-d]pyrimidine-6-carboxylic acid ethyl ester in 50 ml. of dimethylformamide was added 9.35 g. (0.06 mole) of ethyl iodide. The reaction mixture was heated to 50° for 4 hours; cooled in ice and then poured into one liter of water. The reaction mixture was kept in a cold room for 3 days and was then filtered. The product amounted to 3.4 g. (m.p. 230°–231°). The analytical sample was obtained by recrystallization from ethanol.

Analysis for: $C_{13}H_{16}N_4O_3$. Calculated: C, 56.51; H, 5.84; N, 20.28. Found: C, 56.12; H, 5.66; N, 20.09.

Percentage inhbition: 60%.

EXAMPLE 2

5-Amino-8-ethyl-7,8-dihydro-7-oxo-2-propyl-pyrido[2,3-d]pyrimidine-6-carboxylic acid ethyl ester To a solution of 3.4 g. (0.15 g. atom) of sodium in 250 ml. of ethanol was added 24.0 g. (0.15 mole) of diethyl malonate. After a few minutes 8.1 g. (0.05 mole) of 4-ethylamino-2-propyl-5-pyrimidine carbonitrile was added. The reaction mixture was heated under reflux with stirring for 5 hours, during which time the sodium salt of 5-amino-7,8-dihydro-7-oxo-2-propyl pyrido[2,3-d]pyrimidine-6-carboxylic acid ethyl ester precipitated out of solution. This material amounted to 11.3 g.

To a solution containing 5.96 g. (0.02 mole) of the above sodium salt in 50 ml. of dimethylformamide was added 9.36 g. (0.06 mole) of ethyl iodide. The reaction mixture was heated at 50° for 2 hours and was then cooled in ice and poured into 500 ml. of water. The resulting precipitate was collected and amounted to 4.9 g. (m.p. 192°–193°). Recrystallization from ethanol gave 3.0 g. of product, m.p. 199°–200°.

Analysis for: $C_{15}H_{20}N_4O_3$. Calculated: C, 59.19; H, 6.62; N, 18.41. Found: C, 69.19; H, 6.59; N, 18.81.

Percentage inhibition: 29%.

EXAMPLE 3

5-Amino-8-butyl-7,8-dihydro-2-methyl-7-oxopyrido[2,3-d]pyrimidine-6-carboxylic acid ethyl ester To a solution containing 5.4 g. (0.02 mole) of the sodium salt of 5-amino-7,8-dihydro-2-methyl-7-oxopyrido[2,3-d]pyrimidine-6-carboxylic acid ethyl ester in 50 ml. of dimethylformamide was added 4.6 g. of butyl iodide. The reaction mixture was heated to 50° for 3 hours, cooled overnight at room temperature and was then poured into 500 ml. of water. The product was collected on a suction filter giving 5.5 g. of crude product, m.p. 214°–216°. Recrystallization from ethyl acetate afforded 2.9 g. of product, m.p. 220°–222°.

Analysis for: $C_{15}H_{20}N_4O_3$. Calculated: C, 59.19; H, 6.56; N, 18.41. Found: C, 59.13; H, 6.56; N, 18.41.

What is claimed is:

1. A compound of the formula:

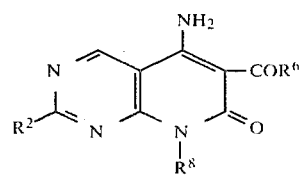

in which
R$^2$ is alkyl of 1 to 6 carbon atoms;
R$^6$ is alkoxy of 1 to 6 carbon atoms, amino, mono- and di-alkylamino where each alkyl group has from 1 to 6 carbon atoms, 2-hydroxyethylamino, 2-alkoxyethylamino of 3 to 8 carbon atoms or 2-(dialkylamino)ethylamino in which each alkyl group has from 1 to 6 carbon atoms; and $R^8$ is alkyl of 1 to 6 carbon atoms;

or a pharmaceutically acceptable salt thereof.

2. The compound of claim 1 which is 5-amino-7,8-dihydro-8-ethyl-2-methyl-7-oxo-pyrido[2,3-d]pyrimidine-6-carboxylic acid ethyl ester.

3. The compound of claim 1 which is 5-amino-8-ethyl-7,8-dihydro-7-oxo-2-propyl-pryido[2,3-d]pyrimidine-6-carboxylic acid ethyl ester.

4. The compound of claim 1 which is 5-amino-8-butyl-7,8-dihydro-2-methyl-7-oxo-pyrido[2,3-d]pyrimidine-6-carboxylic acid ethyl ester.

* * * * *